United States Patent [19]

Suzuki

[11] Patent Number: 4,768,513
[45] Date of Patent: Sep. 6, 1988

[54] METHOD AND DEVICE FOR MEASURING AND PROCESSING LIGHT

[75] Inventor: Susumu Suzuki, Hamamatsu, Japan

[73] Assignees: Agency of Industrial Science and Technology; Ministry of International Trade & Industry, both of Tokyo, Japan

[21] Appl. No.: 31,370

[22] Filed: Mar. 30, 1987

[30] Foreign Application Priority Data

Apr. 21, 1986 [JP] Japan .................................. 61-90149

[51] Int. Cl.$^4$ ........................ A61B 5/00; G01N 21/00
[52] U.S. Cl. .................................. 128/634; 128/665; 250/461.2; 356/73; 356/318
[58] Field of Search ...................... 128/633, 634, 665; 250/461.2; 356/317, 318 X, 73 X

[56] References Cited

U.S. PATENT DOCUMENTS

| | | | |
|---|---|---|---|
| 4,178,917 | 12/1979 | Shapiro | 128/665 |
| 4,556,057 | 12/1985 | Hiruma et al. | 128/634 X |
| 4,718,417 | 1/1988 | Kittrell et al. | 128/634 X |

FOREIGN PATENT DOCUMENTS

59-40830  3/1984  Japan .
59-40869  3/1984  Japan .

Primary Examiner—William E. Wayner
Attorney, Agent, or Firm—Oblon, Fisher, Spivak, McClelland & Maier

[57] ABSTRACT

A method and device for measuring and processing light whereby laser light is irradiated onto positions of an organism which has been injected with a fluorescent substance having a strong affinity for tumors, the fluorescence and the reflected light produced by this irradiation are detected, and the detected intensity of the fluorescence is calculated and analyzed by means of the intensity of the reflected light.

16 Claims, 9 Drawing Sheets

METHOD AND DEVICE FOR MEASURING AND PROCESSING LIGHT

BACKGROUND OF THE INVENTION

1. Field of the Invention

This invention relates to a method and device for measuring and processing light in which organisms previously injected with a hematoporphyrin derivative (hereinafter abbreviated as HPD) or other fluorescent substances which have a strong affinity for tumors are irradiated with laser light at predetermined positions such as the trachea, bladder, etc. in order to produce fluorescent light, and tumors in them are diagnosed by means of the intensity of the fluorescence produced at this time and by the intensity of the reflected light, or in which they are given therapy by irradiation with laser light of another wavelength.

2. Description of the Prior Art

Methods and devices for cancer diagnosis and therapy utilizing the photochemical reactions between laser light and fluorescent substances such as HPD which have a strong affinity for tumors have been proposed (Japanese Patent Application Disclosures Nos. SHO 59-40830 and SHO 59-40869, U.S. Pat. No. 4,556,057).

Figure 1:
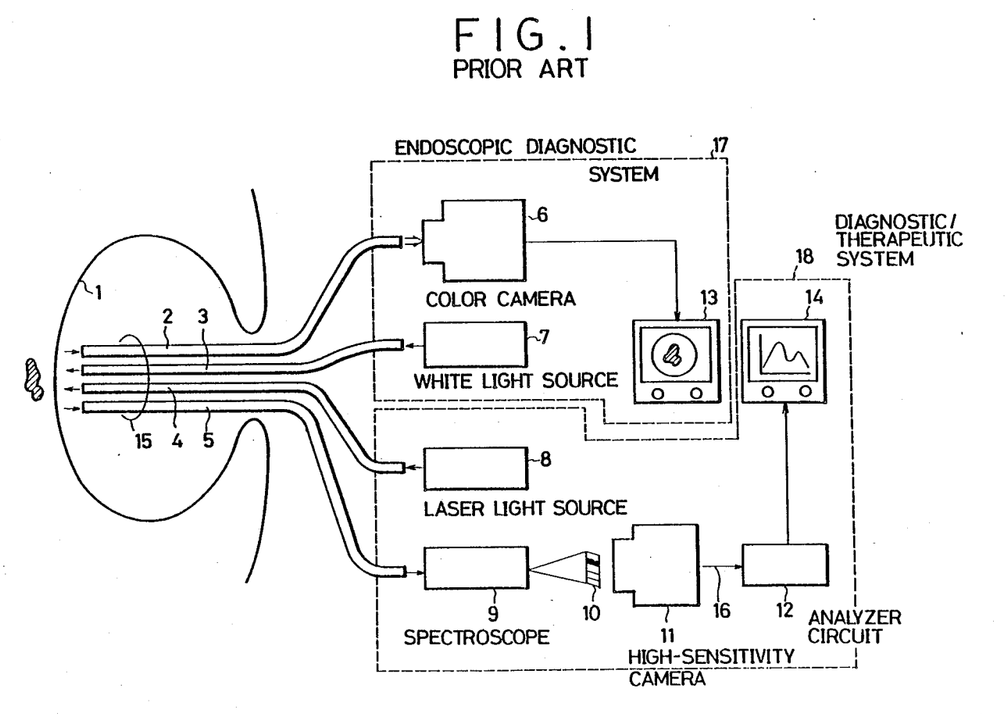
FIG. 1 is a block diagram illustrating an example of a light measuring device of the past.

FIG. 1 is a block drawing illustrating the basic configuration of the diagnostic device of the past.

It can be divided, insofar as the configuration of the device is concerned, into an ordinary endoscopic diagnostic system 17 and a photochemical reaction diagnostic therapeutic system 18. In FIG. 1, a fiber bunch 15 is incorporated in the endoscope and is inserted into the patient's body at the position suspected to be the focus, the patient having been previously given an intravenous injection of HPD.

The endoscopic diagnostic system 17 consists of a white light source 7 for illuminating a tissue surface 1, a light guide 3 conducting this light, an image guide 2 conducting images of the tissue surface 1 to a color camera 6, and a monitor TV 13 for displaying images of the tissue surface 1 picked up by the color camera 6.

The photochemical reaction diagnostic/therapeutic system 18 is equipped with a laser light source 8 which outputs, as pulsed laser light, both laser light for diagnosis (405 nm) and laser light for therapy (630 nm).

The laser light for diagnosis is conducted to the affected part by means of a light guide 4. It is irradiated onto the affected part and excites fluorescence.

The fluorescence produced by the exciting light is conducted by a light guide 5 to a spectroscope 9.

Fluorescence spectrum images 10 obtained from the spectroscope 9 are picked up by a high-sensitivity camera 11, video signals 16 output by it are converted into graphic images by arithmetical processing in an analytical circuit 12, and the images are displayed on a monitor TV 14 as spectrum patterns. The spectrum images 10 are set within the wavelength region of 600–700 nm so that it will be possible to observe the spectrum with two peaks at 630 nm and 690 nm which is a characteristic of HPD fluorescence.

Since endoscopic diagnosis and photochemical reaction diagnosis/therapy are carried out concurrently, the white light source 7 and laser light source 8 irradiate the tissue 1 by a timesharing system. The high-sensitivity camera 11 which picks up the fluorescence spectrum operates intermittently, synchronized with the irradiation of laser light.

Using this device, the operator during diagnosis can locate a cancer while viewing at the same time the tissue images on the monitor TV 13 and the fluorescence spectrum patterns on the monitor TV 14. If a cancer is discovered, the operator can perform therapy immediately by merely switching over the light from exciting light to therapeutic light.

Therapy is carried out by means of a photochemical reaction between the HPD remaining in the cancerous part and the therapeutic light. This causes necrosis selectively at the cancerous part only.

Furthermore, as for the detection of fluorescence during diagnosis, the spectrum patterns which are unique to the fluorescence themselves are observed directly and are not confused with the spontaneous fluorescence emitted from the normal parts themselves. This makes it possible to determine the presence of cancer easily. This may possibly contribute greatly to the diagnosis and therapy of cancer in the early stage, particularly in cases where it is difficult to discover by means of endoscopic diagnosis alone.

As was described above, this device utilizes the affinity of HPD for tumors in the diagnosis and therapy. In actual fact, diagnosis is performed after waiting for two or more days after injection of the HPD until such time as the difference in concentration of the residual HPD between normal cells and cancerous cells reaches a ratio of about 1:10, the exact time differing somewhat depending upon the organ in which one is interested. Consequently, the detection of fluorescence does not in itself indicate the presence of cancer, and the intensities must be distinguished in order to determine whether or not cancer is present.

Furthermore, when the area of the cancerous part is smaller than the area irradiated with exciting light (the diameter of the latter ordinarily ranges from several mm to 10 mm), even though the concentration ratio of the residual HPD may be 1:10, the differences in the detected intensity of the fluorescence attributable to the presence or absence of cancer will be far smaller.

For example, if we assume that the amount of fluorescence is directly proportional to the HPD concentration, the ratio between the fluorescent intensity when a cancer 1 mm in diameter is present within an irradiated range 5 mm in diameter will become quite close to the fluorescent intensity when such a cancer is absent, the ratio amounting in this case to about 1.36:1.

The following fluctuating factors may also be mentioned as items making this discrimination even more difficult:

(1) Power fluctuations of the laser light (2) Fluctuations in the relative positions of the irradiating fiber opening and the irradiated surface (3) Fluctuations in the relative positions of the fluorescent part (the irradiated surface) and the detecting fiber opening (4) Fluctuations of the effective detection area of the detecting fiber due to shaking of the irradiating fiber (that is, shaking of the irradiating position)

As for factor (1) above, there are instantaneous power fluctuations of about 5–10% in light sources which combine an excimer laser with a dye laser, such as those which were used in the past example mentioned above.

Factors (2)–(4) are fluctuations due to manipulation of the endoscope. On account of factor (2), the density of the exciting light irradiated onto the tissues varies in inverse proportion to the square of the distance.

On account of factor (3), of the fluorescence produced, the percentage which enters the detecting fiber varies in inverse proportion to the square of the distance. In addition, since the irradiation area and focusing area also vary in accordance with fluctuations of factors (2) and (3), one may assume that factors (2) and (3) taken together will cause the detected intensity of the fluorescence to fluctuate approximately in inverse proportion to the square of the distance.

In factor (4), shaking of the irradiating fiber is caused by the following. That is, deterioration of the irradiating fiber tends to be brought about by the strong pulsed light, ordinarily with a repeated frequency of several tens of hertz and a peak power of about 1 megawatt, which passes through the fiber. A condition for mounting irradiating fiber in an endoscope is that the fiber must be easily replaceable. Thus, inserting the fiber into the forceps opening of the endoscope is the easiest method for mounting and removing it, and this is the method in general use.

However, when this method is used, the aforementioned shaking occurs because of manipulation of the endoscope, particularly when the endoscope is bent, because the irradiating fiber and the endoscope do not form an integrated whole. Discrepancies between the irradiating position and the field of observation of the fluorescence detecting fiber occur as a result. This causes fluctuations of the effective detection area of the fluorescent light, and the detected intensity of the fluorescence also fluctuates.

The fluctuating factors explained above are all superimposed on each other and influence the detected intensity of the fluorescence. This leads to certain problems. For example, stronger fluorescence may be detected from nearby normal cells than from more distant cancerous cells; or, even when the exciting light is irradiated on cancerous cells, its fluorescence may not enter the field of the detecting fiber, and an intense fluorescence spectrum may not be observed at all. These problems make it exceedingly difficult to determine whether or not cancer is present.

In connection with problems of this type, the following is a technology which has been used in controlling items such as the light source for illumination in endoscopes of the past. In this technology, another fiber is used to detect the reflected light of the light irradiated from the light source through the fiber, and the amount of light output from the light source is controlled in accordance with the amount of light detected by this other fiber. Thus, the amount of irradiated light is kept constant.

Nevertheless, the following inconveniences result when an attempt is made to apply this method for resolving the aforementioned problems.

First of all, because of the delay factor which is inherent in the feedback control system, the fluctuating factors cannot be compensated for at every pulse of the irradiated laser light.

Second, it is difficult to control the output of pulsed lasers with a good precision throughout a range amounting to multiples of about 10, and to control it with a time constant approximately equivalent to the blurring of the endoscope.

Third, concerning the aforementioned fluctuating factor (4), when the irradiation position has departed from the field of detection, control will be difficult, and it is also possible that excessive amounts of light will be irradiated. Given the control performance which is required in medical equipment, it would seem to be quite difficult to realize the needed improvements.

SUMMARY OF THE INVENTION

The purpose of this invention is to provide a device and method for measuring and processing light which goes far in eliminating the uncertain factors which interfere with quantification of the fluorescence excited and which are caused, for example, by power fluctuations of the laser light for excitement or by fluctuations of the relative positions of the irradiating and detecting fibers and the organism's tissues.

In order to achieve the aforementioned purpose, the method and device according to this invention comprise a method and device for measuring and processing light in which laser light for producing fluorescence is irradiated onto predetermined positions of an organism which has previously been injected with a fluorescent substance having a strong affinity for tumors, and the intensity of the fluorescence thus produced is detected. This device consists of a light-irradiating device which irradiates the organism with the aforementioned laser light, a light-detecting device which detects and outputs the fluorescence produced by the organism upon excitement by the aforementioned laser light as well as the aforementioned laser light reflected from the organism, and an analyzer unit into which the output signals of this light-detecting device are input and the intensity of the aforementioned fluorescence is calculated and analyzed in terms of the intensity of the reflected light.

In other words, the device and method according to this invention are provided with functions whereby the same fibers are used for detecting, not only the fluorescence generated when the organism's tissues are irradiated with laser light, but also the laser light reflected from the tissues at this time, and whereby the intensity of the fluorescence is calculated and analyzed by means of the intensity of this reflected light.

Furthermore, when the detected intensity of the reflected light is extremely weak, this indicates that there is insufficient irradiation within the field of the detecting fiber. Therefore, the device can be configured so that, when such a condition exists, this information can be displayed in a suitable form.

Other purposes and characteristics of this invention will be clarified in the ensuing detailed explanation on the basis of the attached drawings.

DETAILED DESCRIPTION OF THE PREFERRED EMBODIMENT

Figure 2:
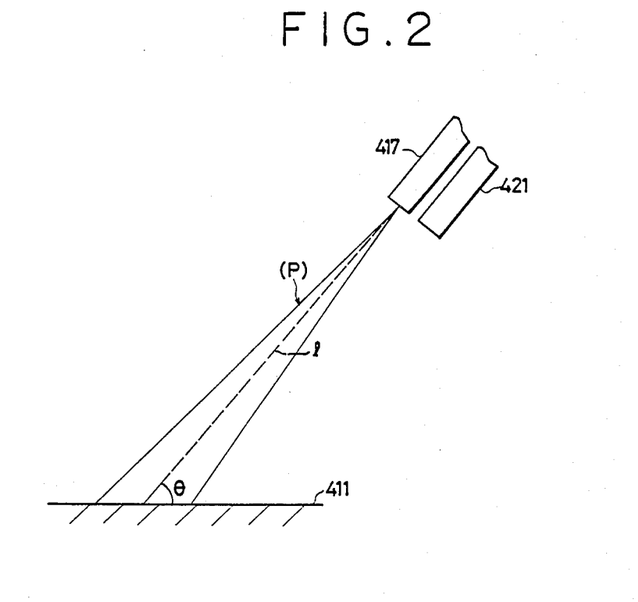
FIG. 2 is an explanatory view illustrating the positional relationship between the pair of fibers, the irradiating fiber and the detecting fiber, and the tissues.
Figure 3:
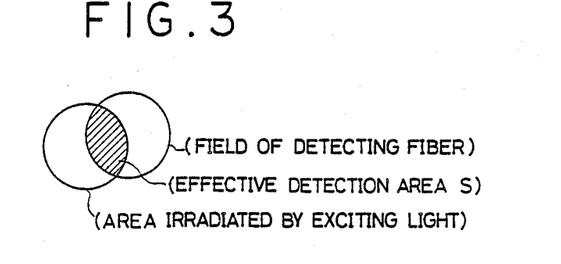
FIG. 3 is a schematic diagram illustrating the relationship between the irradiated area by the exciting light and the field of the detecting fiber.

First we shall use FIGS. 2 and 3 to explain the basic principles of this invention, in particular the meaning of the calculations and analyses.

In FIG. 2, the irradiating fiber 417 is in a position with a distance $l$ and an angle $\theta$ from the irradiated surface. Pulsed laser light of P (joules per pulse) is emitted from here towards the surface of the organism's tissues.

The intensity Iin of the incident laser light on the tissues will be a function of the aforesaid fluctuating factors P, $l$ and $\theta$, and $$Iin = Iin\,(P, l, \theta)$$

The amount of fluorescence IF generated by this laser light will be:

$$IF = k_0 \cdot Iin \cdot \eta F \cdot n$$

$k_0$: Constants unrelated to P, $l$ and $\theta$
$\eta F$: Fluorescent efficiency of HPD
n: HPD concentration Although the amount of fluorescence IF is not in a strictly proportional relationship with the HPD concentration (n), an approximately proportional relationship applies with reference to the actual value of $n(10^{-5}-10^{-6}\,\text{mol/l})$.

If the amount of the fluorescence produced IF which enters the detecting fiber is If, and if the efficiency with which fluorescence is detected by the detecting fiber is $\eta D$, then $$\begin{aligned}If &= IF \cdot \eta D \\ &= k_0 \cdot Iin \cdot \eta F \cdot n \cdot \eta D\end{aligned}$$

$\eta D$ will be a function of the relative positions of the fluorescent part and the detecting fiber ($l$, $\theta$) and of the effective detection area S shown in FIG. 3.

S fluctuates as a result of the aforementioned shaking of the irradiating fiber.

$$\eta D = \eta D(l, \theta, S)$$

Since the orientation of fluorescence is isotropic, it is not included as a function within $\eta D$.

The reflected light Ir entering the detecting fiber is given by the following:

$$Ir = k_1 \cdot Iin \cdot R \cdot \eta'D$$

$k_1$: A constant unrelated to P, $l$, $\theta$
R: Reflection ratio
$\eta'D$: Detection efficiency of reflected light The reflection ratio R will strictly be a function of n, but it can be regarded as more or less constant with respect to the actual value of n, which is an extremely thin concentration, and will have a value determined by the properties of the tissues.

The following can be said about the comparison between $\eta D$ and $\eta'D$.

First, since the place where both the reflected light and the fluorescence are produced is the position irradiated with the laser light, and since the same detecting fiber is used, the geometrical conditions are exactly the same.

As for the orientation of the reflected light, the scattered reflected light (excluding the surface reflected light) is isotropic, like the fluorescence. Therefore, if it alone is separated and detected by means of a polarizing filter, the orientation conditions will be the same.

Consequently, $\eta D = \eta'D$ will be realized.

Incidentally, the difference in the field of detecting fiber due to differences in wavelength between the reflected light (405 nm) and the fluorescence (630 nm) is slight and may be regarded as a fixed factor. Therefore, no practical problem arises on account of this difference.

Consequently, it follows that:

$$Ir = k_1 \cdot Iin \cdot R \cdot \eta D$$

If the detected intensity of the fluorescence If is divided by the detected intensity of the reflected light Ir:

$$If/Ir = k_2 \cdot \eta F \cdot n / R$$

$k_2$ is $(k_0/k_1)$, a constant unrelated to P, $l$ and $\theta$.

Thus, If/Ir will be directly proportional both to the fluorescent efficiency of HPD ($\eta F$) and to the HPD concentration (n) and inversely proportional to the reflection ratio of the organism' tissues. Thus, the fluctuating factors P, $l$, $\theta$ and S can be eliminated during diagnosis. That is all of the fluctuations of the detected intensity of the fluorescence due to these factors can be compensated for.

Since the value of Ir itself is proportional to the intensity of the laser light irradiated inside the field of the detecting fiber, it is not desirable from the diagnostic point of view for Ir to be extremely weak. On the contrary, when an excessively intense reflected light Ir is detected, this means that excessive laser light is likewise irradiated onto the tissues. Therefore, if this is continued it may possibly lead to inflammation or the like in the organism's tissues.

Therefore, the operator can obtain important information about these matters if abnormalities of Ir are displayed, for example on the monitor TV.

This greatly improves the performance of the device as medical equipment.

Next let us explain the light measuring device of this invention by referring to the drawings.

Figure 4:
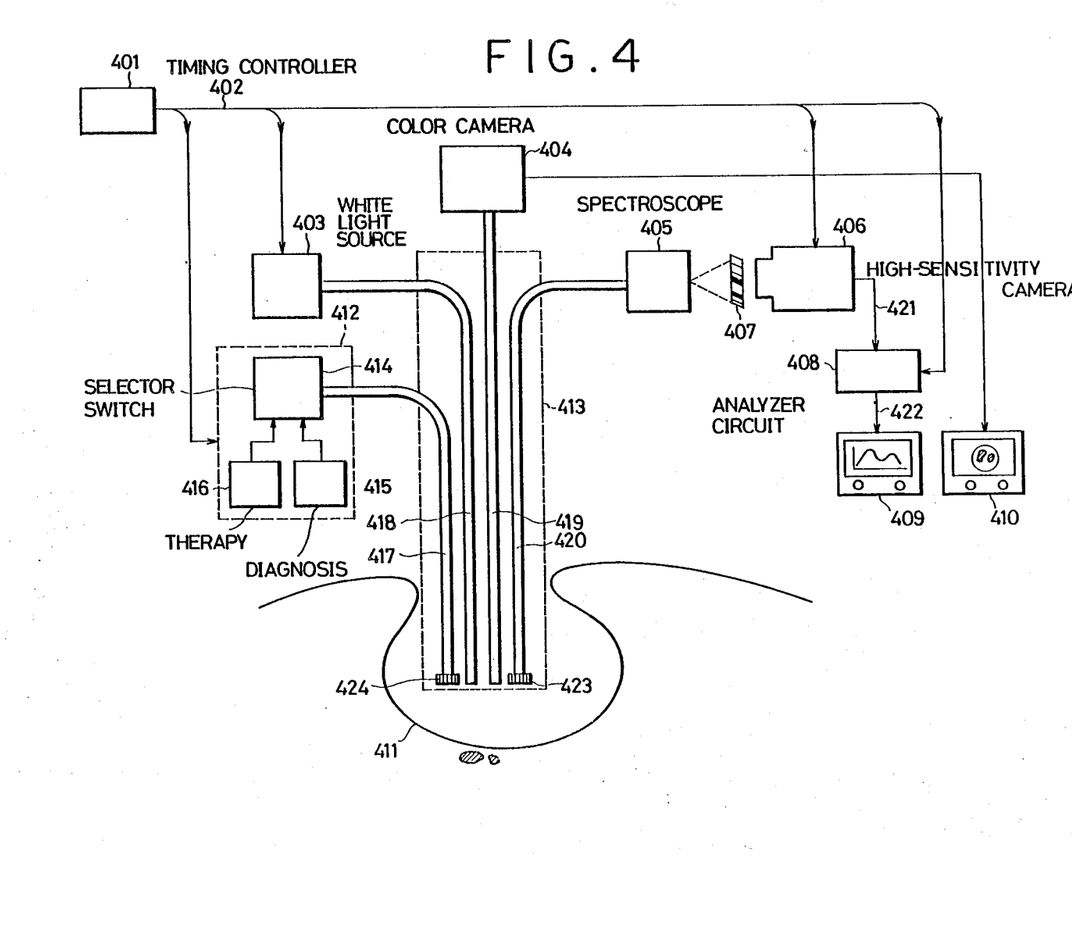
FIG. 4 is a block diagram illustrating an embodiment of a light measuring/processing device according to this invention.

FIG. 4 is a block diagram illustrating an embodiment of a light measuring/processing device according to this invention. The endoscope 413 has been inserted into the patient's body at the position suspected to be the focus, the patient having been previously given an intravenous injection of HPD. The light guides 417, 418 and 420 and the image guide 419 are mounted on the endoscope 413.

Light guide 418 conducts light from the white light source 403 to the affected part and illuminates the tissues 411. Images of the illuminated tissues are conducted by image guide 419 to the color camera 404, and pictures of them are displayed on the monitor TV 410. The operator, viewing them, confirms the position and performs a qualitative visual diagnosis of the tissues.

On the other hand, the first laser light for diagnosis and the second laser light for therapy from the laser light source 412 pass through light guide 417 and are irradiated onto the tissues 411. A polarizing filter 424 is provided on the tip of the light guide 417.

The laser light source 412 consists of a laser light source for therapy 416, a laser light source for diagnosis 415, and a switching device 414. The operator can switch the output light depending upon whether it is intended for diagnosis or therapy.

Light guide 420 is an optical fiber for detecting fluorescence and reflected light from the organism's tissues. In order to prevent surface reflection components from mixing into the reflected light, polarizing filter 424 whose polarizing direction is orthogonal to that of polarizing filter 423 is mounted at the light inlet of light guide 420. Light guide 420 is conducted to the spectroscope 405. Spectrum images 407 of 400-700 nm, including both the reflected light and fluorescence, are output from the spectroscope 405.

Figure 5:
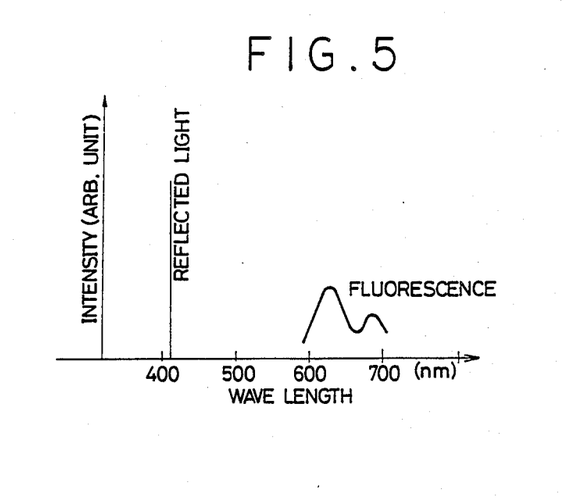
FIG. 5 is a graph illustrating a spectrum of the detected light.

FIG. 5 is a graph illustrating an example of such a spectrum.

Since the spectrum images have an extremely weak intensity, a high-sensitivity camera 406 is used to pick up them.

In order to adjust the intensity balance between the reflected light and the fluorescence, a filter to reduce the intensity of reflected light (405 nm) is mounted as necessary on the light inlet of the high-sensitivity camera 406.

The video signals 421 output by the high-sensitivity camera are input into the analyzer circuit 408. Here the intensity of the fluorescence is calculated and analyzed by means of the intensity of the reflected light included as information within the video signals 421, and this is converted into graphic images consisting of the spectrum patterns. They are output to the monitor TV 409.

The value of the intensity of the reflected light itself is also converted into graphic images of a suitable form in the analyzer circuit 408, and they are displayed on the monitor TV 409.

This display indicates the state when the field of the detecting fiber 420 (the detection area) contains either too little or too much exciting light irradiated onto the tissues. The former indicates that the minimum light necessary for diagnosis is not being irradiated, while the latter indicates that the amount of light being irradiated is excessive for the tissues.

Endoscopic diagnosis through monitor TV 410 and fluorescent diagnosis by monitor TV 409 are both performed concurrently. For this reason, the white light source 403 and the laser light source 412 illuminate the tissues by a timesharing system so that the white light for illumination will not influence the fluorescence spectrum. Moreover, the picking up of the spectrum image by the high-sensitivity camera 406 is synchronized with the irradiation of the exciting light, and the shutter remains closed during other periods in order to protect it from the intense white light.

Figure 6:
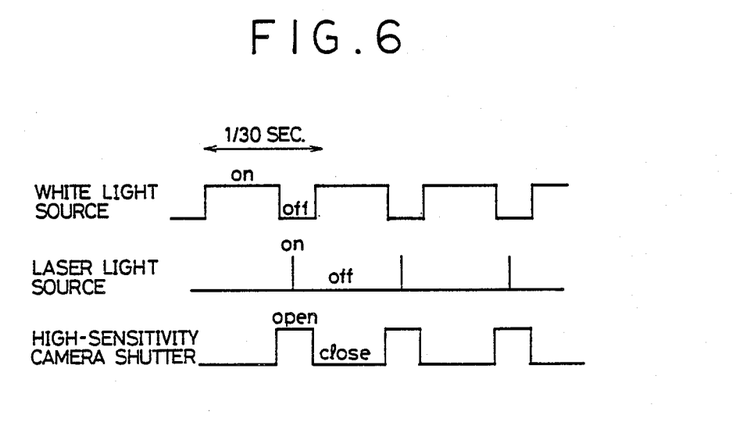
FIG. 6 is a timing chart illustrating the operation of the device.

FIG. 6 is a timing chart of the operations of the white light source 403, the laser light source 412, and the high-sensitivity camera 406. The operating period is set at 1/30 second, synchronized with the frame frequencies of television. The timing signals 402 needed in these operations are supplied from the timing controller 401.

The characteristic differences between this embodiment and the past example illustrated in FIG. 1 are the fact that the range of the spectrum images 407 includes the reflected light (405 nm) as well, the contents of the processing performed in the analyzer circuit 408, and the contents of the display of monitor 409. Of these, let us explain in detail the configuration of the analyzer circuit 408, which will be a key point in signal processing.

Figure 7:
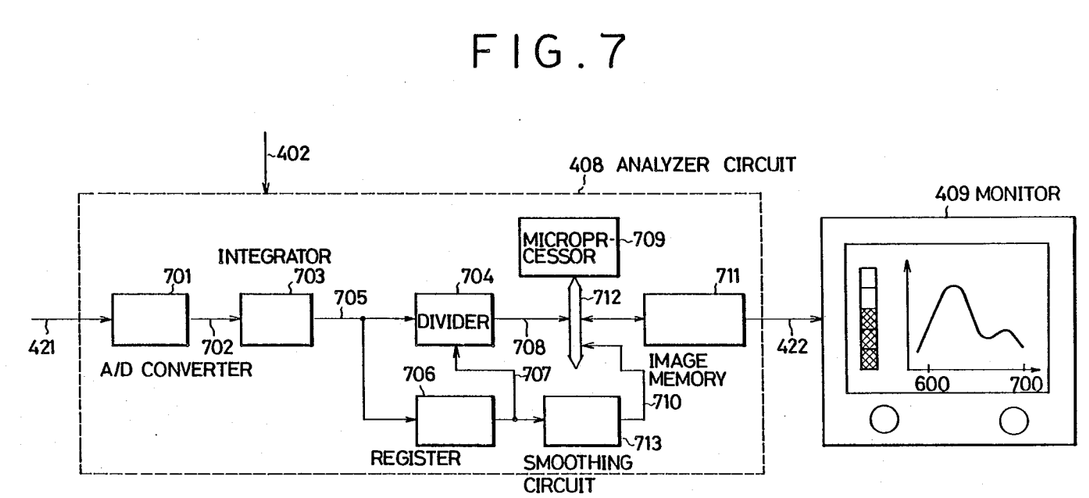
FIG. 7 is a block diagram illustrating the configuration of the analytical circuit.
Figure 8:
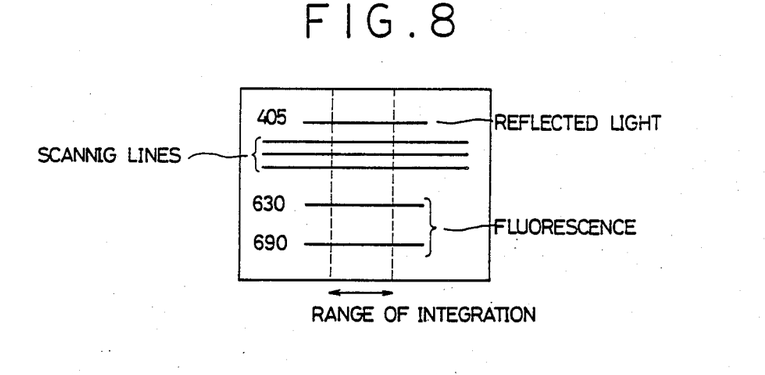
FIG. 8 is a view illustrating the spectrum image picked up.

FIG. 7 illustrates the configuration of the analyzer circuit 408. The video signals 421 input into the analyzer circuit 408 are the output signals when the spectrum images 407 were scanned and picked up by the high-sensitivity camera 406 in parallel with the spectral lines, as is shown in FIG. 8.

Consequently, the signal amplitude of a particular scanning line corresponds to the intensity of light of a specific wavelength. The video signals 421 are converted into 8-bit digital video signals 702 by the A/D converter 701. The digital video signals 702 are integrated for each scanning line by an integrator circuit 703 over a range where effective spectrum images are present, as is shown in FIG. 8. This makes it possible to improve the S/N ratio of the signals.

Integrated values 705 corresponding to the intensity at each wavelength are outputted for each scanning period from the integrator circuit 703. These signals for the integrated values 705 are input into a divider 704 and register 706. The register 706 samples the signals for the integrated values 705 when they are the values of the reflected light (405 nm) and holds them as signals for the intensity of the reflected light 707 in the output. The divider 704 divides the signals for the integrated values 705 corresponding to the fluorescent region (600-700 nm) by the signals for the intensity of the reflected light 707, which are already kept in a state of hold. In this way, the fluorescence is calculated and analyzed by means of the reflected light, and unwanted fluctuating factors are eliminated from the detected intensity of the fluorescence.

The normalized fluorescence signals 708 which are output by the divider 704 are input through bus line 712 into the microprocessor 709. Here they are processed to convert them into graphic images, and the spectrum images are written into the image memory 711 through bus line 712.

The signals for the intensity of the reflected light 707 are updated to new data when the tissues are irradiated with laser light and new information on the reflected light is output from the integrator 703. Consequently, its period is also 1/30 second, the same as that of the laser irradiation.

So, if the signal 707 itself is used as a warning signal which indicates the excessively large or excessively small irradiation to the tissue, its sensitivity will be much higher than that of ordinary signal, because the signal 707 follows the instantaneous change of each laser pulse whose repetition rate is 1/30 sec. Consequently, in this embodiment there is provided a smoothing circuit 713 to realize a relaxation time constant of about 2 seconds to the signals 707 for the intensity of reflected light.

Figure 9:
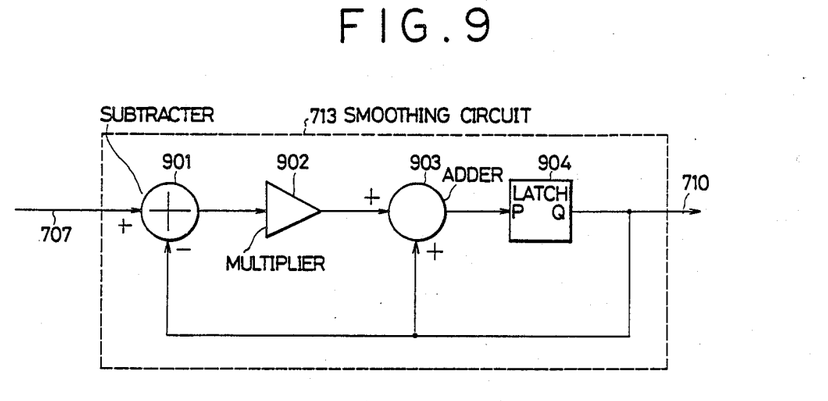
FIG. 9 is a circuit view illustrating an embodiment of a smoothing circuit.

Its output is sent through bus line 712 to the microprocessor 709, where it is given graphics processing, and the results are written into the image memory 711. FIG. 9 is an example of a configuration of the smoothing circuit 713. A subtracter 901 subtracts the output signals 710 from the input signals 707, the results are multiplied by 1/k by a multiplier 902, and these results are then added again to the signals 710 by an adder 903. These results are input into a latch 904. The latch 904 performs latch operations synchronized with changes of the input signals 707.

The smoothing circuit with this configuration has transfer characteristics similar to those of a first stage CR low-pass filter in an analog circuit. Its time constant is given by Ts.k (Ts is the variation period of the input signals). In this embodiment, the values are set at $Ts=1/30$ second and $k=2^6$, and a time constant of about 2 seconds has been realized.

The fluorescence spectrum graphics and the graphics for the intensity of reflected light which have been processed by the microprocessor 709 are written in the image memory. They are read out in synchronization with the television signals and are displayed on the monitor TV.

In this embodiment, as is shown in FIG. 7, the intensity of the reflected light is displayed in level meter format. This display was adopted so that the display color would be changed whenever the values entered the excessively large or excessively small region in order to attract the operator's attention.

Next let an example of a test of this invention will be explained.

Figures 10, 11:
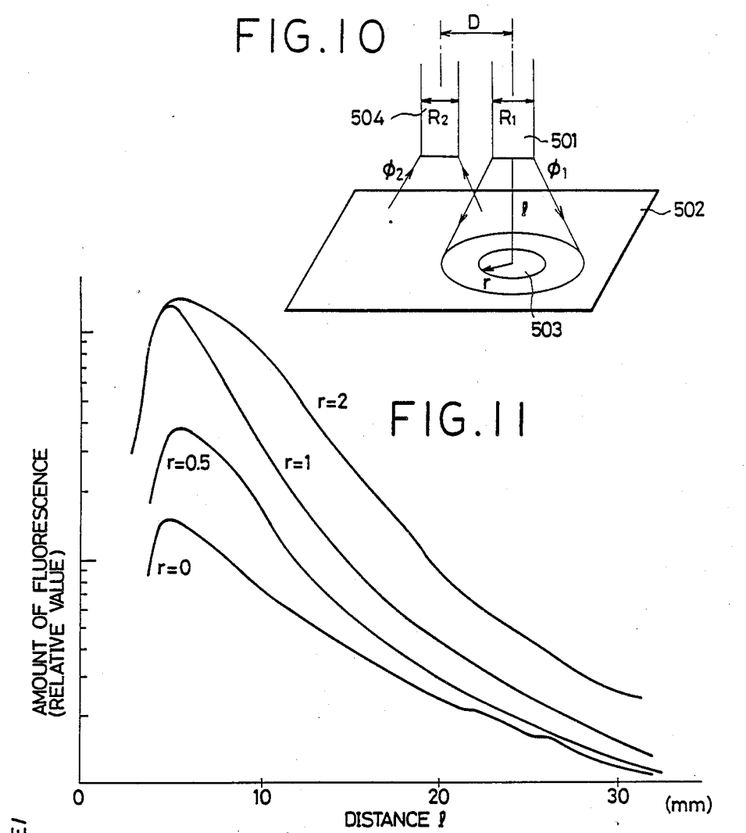
FIG. 10 is an explanatory view of the basic principles of calculation.
FIG. 11 is a graph illustrating the calculation result of the amount of detected fluorescence.

FIG. 10 is an explanatory view of the basic principles of calculation when the amount of fluorescence detected is calculated by computer simulation. The light receiving surface 502 was fixed at a position at a distance l (mm) away from the light guide 501 for laser light, and a hypothetical cancer 503 with a radius r (mm) was assumed to be present on this light receiving surface 502. The detecting light guide 504 for detecting fluorescence and reflected light is located parallel to the light guide 501 for laser light at a distance D away from it. The values of geometrical parameters in endoscopes which are used in actual devices are used for the fixed parameters $R_1$, $R_2$, D, $\phi_1$ and $\phi_2$ in the calculations.

| | | |
|---|---|---|
| $R_1$ | Diameter of light guide 501 | 0.4 mm |
| $R_2$ | Diameter of light guide 504 | 1.4 mm |
| D | Distance between light guides 504 and 501 | 2 mm |
| $\phi_1$ | Laser irradiation angle | 23° |
| $\phi_2$ | Detection angle of fluorescence, reflected light | 25° |

The difference in fluorescence efficiency between the cancerous part and the normal parts was assumed to be a ratio of 10:1.

FIG. 11 gives the curves obtained when the amount of fluorescence detected was calculated when $r=0$, $r=0.5$, $r=1$, and $r=2$ in the explanatory view of the basic principles of calculation in FIG. 10, with l plotted on the abscissa.

Figure 12:
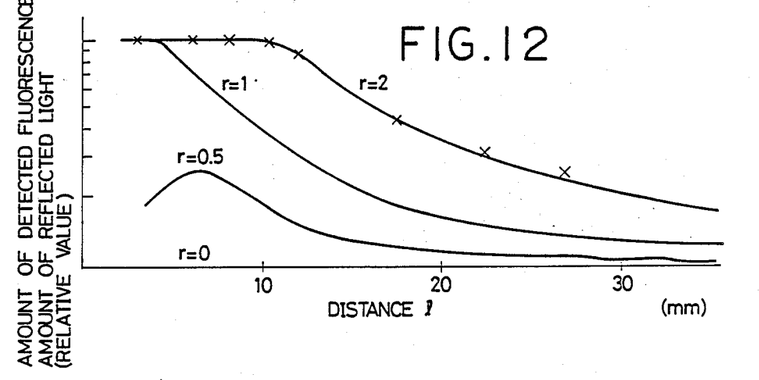
FIG. 12 is a graph illustrating the amount of detected fluorescence normalized by the amount of detected reflected light.

FIG. 12 gives a graph obtained when other curves were normalized (divided) by the curve for $r=0$ shown in FIG. 11 above. As one would naturally assume, in FIG. 12, the graph of $r=0$ is always a straight line at 1.

The graph of $r=0$ in FIG. 11 shows, in model terms, the changes due to l when uniform fluorescence is detected from normal tissues. As was mentioned above, these are exactly the same as the changes when scattered reflected light is detected from tissues having a uniform reflectivity. Consequently, the graph in FIG. 12, normalized by the graph for $r=0$, will indicate the changes which will occur when fluorescence is normalized by the reflected light.

A comparison of FIG. 11 and FIG. 12 seems to indicate that the effects of normalization are the following:

(1) The usual range for the value of l in the human body is several mm to 20 mm. Within this range, values which are proportional to $l^{-3}-l^{-4}$ in FIG. 11 will be proportional to about $l^{-1}$ in FIG. 12. Thus, the fluctuations are reduced greatly.

(2) In FIG. 11, there are frequent cases where the fluorescence from normal cells viewed from positions nearby (for example, the value at $r=0$ mm and $l=10$ mm) displays stronger values than the fluorescence from cancerous cells viewed from a distance (for example, the value at $r=0.5$ mm and $l=15$ mm). However, in FIG. 12, the graph for $r=0$ will always be smaller than the graphs for $r\neq0$. The aforesaid fact is extremely advantageous when diagnosing cancer.

Figure 13:
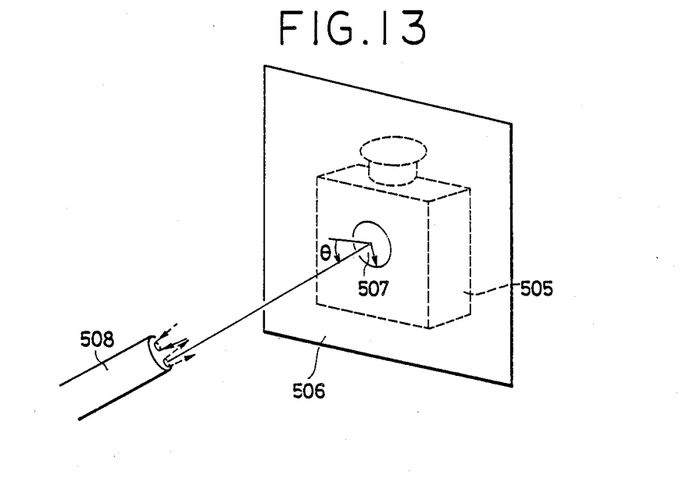
FIG. 13 is a schematic view of test measurements of the amount of fluorescence when r=2.

FIG. 13 is a schematic view of test measurements when a black sheet 506 was put in front of a transparent case 505 containing an HPD solution, a hole 507 with a radius r (mm) was formed in this black sheet 506, and the light guides 508 were installed at a distance l (mm). When r was set at 2 mm, and $\theta$ at 0° and the detected intensity of the fluorescence was actually measured, the measured values shown by the circles in FIG. 15 were obtained, with l plotted on the abscissa. The solid curve plotted on these measured values plots the calculated values obtained under condition where $r=2$ mm and $\theta=0°$.

Figure 14:
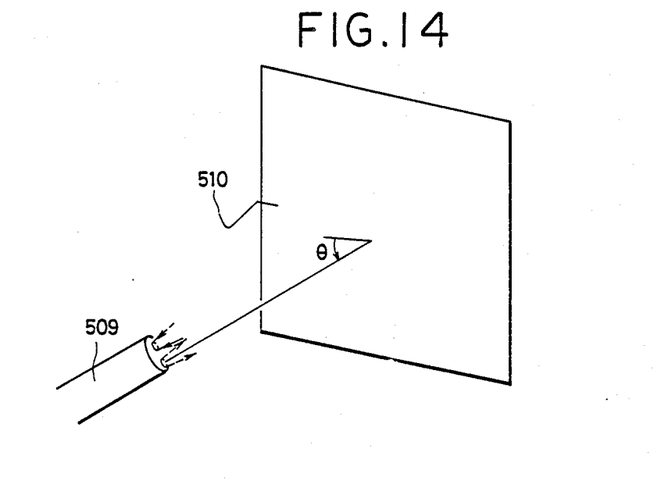
FIG. 14 is a schematic view of test measurements of the reflected light.

FIG. 14 is a schematic view of test measurements of the reflected light when a frosted glass 510 for scattering and reflecting the laser light was positioned at a distance l (mm) away from the light guides 509. The measured values marked with X's in FIG. 15 were obtained when $\theta$ was set at 0° and the reflected light was actually measured. The solid curve plotted on these measured values plots the calculated values obtained under conditions where $r=0$ mm and $\theta=0°$.

Figure 15:
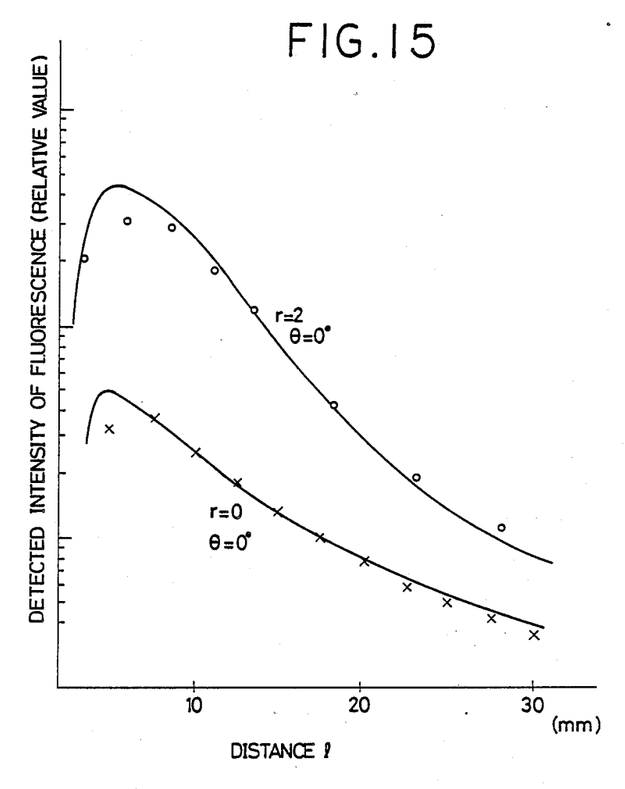
FIG. 15 is a graph plotting the detected intensity in the test results.

As can be understood from FIG. 15, the calculated values and measured values agree within the range of measurement errors under each of the conditions. Let us also compare the calculated values and measured values in cases where the detected amount of fluorescence was normalized by the detected amount of reflected light.

The data marked with X's in FIG. 12 are the values obtained when the measured values at $r=2$ given in FIG. 15 were normalized by the measured values at $r=0$. The corresponding solid curve plots the calculated results.

In this way, it is also clear with respect to the normalized values that their measured values and calculated values agree within the range of measurement errors.

To summarize the above, in this invention it is possible to measure the fluorescence without being influenced by matters such as variations of the laser light or changes in the detected intensity of the fluorescence due to the relative position of the pair of light guides with respect to the organism's tissue. Consequently, even tiny cancer cells can be diagnosed accurately by detecting the fluorescence and can be treated by irradiating the affected parts with therapeutic laser light.

What is claimed is:

1. A method for measuring light, comprising the steps of:
   injecting an organism with a fluorescent substance having a strong affinity for tumors,
   irradiating predetermined positions of said organism with laser light to excite fluorescence and allow said laser light to reflect from said predetermined positions of said organism,
   detecting said fluorescence and reflected light, and
   calculating and analyzing the intensity of the detected fluorescence based on the intensity of the detected light.

2. A method according to claim 1, wherein said fluorescent substance is a hematoporphyrin derivative and said laser light has a wavelength of about 405 nm.

3. A device for measuring light, comprising:
   a light-irradiating means for irradiating with laser light predetermined positions of an organism injected with a fluorescent substance having a strong affinity for tumors,
   a light-detecting means for detecting fluorescence excited by the irradiation of said laser light and laser light reflected by said predetermined positions of said organism, and
   an analyzer means for calculating and analyzing the intensity of said fluorescence based on the intensity of said reflected light.

4. A device according to claim 3, wherein said light-irradiating means comprises a light source for said laser light and a first light guide for transmitting this laser light.

5. A device according to claim 3, wherein said light-detecting means comprises a second light guide for transmitting the reflected light and fluorescence output from the organism, a spectroscopic means for dividing the light transmitted from said second light guide into fluorescence and laser light and outputting them as spectral images, and a pickup means for picking up said spectral images and outputting them as spectral video signals.

6. A device according to claim 3, wherein said light-irradiating means comprises a light source for said laser light and a first light guide for transmitting said laser light, and said light-detecting means comprises a second light guide for transmitting the reflected light and fluorescence output from said organism, a spectroscopic means for dividing the light transmitted from said second light guide into fluorescence and laser light and outputting them as spectral images, and a pickup means for picking up said spectral images and outputting them as spectral video signals.

7. A device according to claim 6, wherein said first light guide has a first polarizing filter mounted at its tip, and said second light guide has a second polarizing filter mounted at its tip so as to have a polarizing direction which is orthogonal to the polarizing direction of said first light guide.

8. A device according to claim 3, wherein said analyzer means is adapted to receive input of spectral video signals, normalize the amplitudes of said signals by arithmetic processing on the basis of information contained in said signals on the intensity of the reflected light, convert the normalized amplitudes into graphic images, display fluorescence spectrum patterns on a monitor and, when said reflected light has dropped below a first standard value or has risen above a second standard value, also display this information.

9. A method for measuring and processing light, comprising the steps of:
   injecting an organism with a fluorescent substance having a strong affinity for tumors,
   irradiating predetermined positions of said organism with first laser light to excite fluorescence and allow said first laser light to reflect from said predetermined positions of said organism,
   detecting said fluorescence and reflected light, and
   calculating and analyzing the intensity of the detected fluorescence based on the intensity of the detected light and, depending on the calculated and analyzed results, irradiating said predetermined positions of said organism with a second laser light to perform processing of said predetermined positions of said organism.

10. A method according to claim 9, wherein said fluorescent substance is a hematoporphyrin derivative, and said first laser light has a wavelength of about 405 nm.

11. A device for measuring and processing light, comprising:
    a light-irradiating means for irradiating with first laser light predetermined positions of an organism injected with a fluorescent substance having a strong affinity for tumors,
    a light-detecting means for detecting fluorescence excited by the irradiation of said first laser light and first laser light reflected by said predetermined positions of said organism,
    an analyzer means for calculating and analyzing the intensity of said fluorescence based on the intensity of said reflected light, and
    a second irradiating means for irradiating said predetermined positions of said organism with second laser light depending on the calculated and analyzed results.

12. A device according to claim 11, wherein said first light-irradiating means comprises a light source for said first laser light and a first light guide for transmitting said first laser light.

13. A device according to claim 11, wherein said light-detecting means comprises a second light guide for transmitting the reflected light and fluorescence output from said organism, a spectroscopic means for dividing the light transmitted from said second light guide into fluorescence and laser light and outputting them as spectral images, and a pickup means for picking up said spectral images and outputting them as spectral video signals.

14. A device according to claim 11, wherein said first light-irradiating means comprises a light source for said first laser light and a first light guide for transmitting said first laser light, and said light-detecting means comprises a second light guide for transmitting the reflected light and fluorescence output from said organism, a spectroscopic means for dividing the light transmitted from said second light guide into fluorescence and laser light and outputting them as spectral images, and a pickup means for picking up said spectral images and outputting them as spectral video signals.

15. A device according to claim 14, wherein said first light guide has a first polarizing filter mounted at its tip, and said second light guide has a second polarizing filter mounted at its tip so as to have a polarizing direction which is orthogonal to the polarizing direction of said first light guide.

16. A device according to claim 11, wherein said analyzer means is adapted to receive input of spectral video signals, normalize the amplitudes of said signals by arithmetic processing on the basis of information contained in said signals on the intensity of the reflected light, convert the normalized amplitudes into graphic images, display fluorescence spectrum wave patterns on a monitor and, when said reflected light has dropped below a first standard value or has risen above a second standard value, also display this information.

* * * * *